(12) United States Patent
Brown et al.

(10) Patent No.: US 8,360,061 B2
(45) Date of Patent: Jan. 29, 2013

(54) PORTABLE BREATHING DEVICE

(75) Inventors: Roger Leslie Brown, London (GB); David Paul Sumners, Stockton-on-Tees (GB)

(73) Assignee: High Tech Health, Ltd., Surrey (GB)

( * ) Notice: Subject to any disclaimer, the term of this patent is extended or adjusted under 35 U.S.C. 154(b) by 1362 days.

(21) Appl. No.: 11/845,916

(22) Filed: Aug. 28, 2007

(65) Prior Publication Data

US 2008/0053456 A1  Mar. 6, 2008

(30) Foreign Application Priority Data

Sep. 5, 2006 (GB) .................................. 0617349.6

(51) Int. Cl.
*A62B 9/00* (2006.01)
*A62B 9/02* (2006.01)
*A62B 9/06* (2006.01)

(52) U.S. Cl. ......... 128/205.24; 128/204.18; 128/204.21; 128/207.14; 128/207.16

(58) Field of Classification Search ............. 128/205.24, 128/204.18, 204.21, 207.14, 207.16
See application file for complete search history.

(56) References Cited

U.S. PATENT DOCUMENTS

| | | | |
|---|---|---|---|
| 1,459,478 A * | 6/1923 | Page ........................ 128/203.24 |
| 5,630,411 A * | 5/1997 | Holscher .................. 128/205.24 |
| 6,083,141 A | 7/2000 | Hougen | |
| 6,302,105 B1 * | 10/2001 | Wickham et al. ........ 128/204.18 |
| 6,581,596 B1 | 6/2003 | Truitt et al. | |
| 6,708,690 B1 * | 3/2004 | Hete et al. ................ 128/204.18 |
| 6,776,159 B2 * | 8/2004 | Pelerossi et al. ......... 128/204.18 |
| 2004/0000310 A1 | 1/2004 | Wickham et al. | |
| 2006/0279085 A1* | 12/2006 | Lee .............................. 290/1 E |

FOREIGN PATENT DOCUMENTS

| | | |
|---|---|---|
| EP | 1103287 A3 | 2/2003 |
| FR | 2744922 A1 | 2/1996 |
| GB | 2196858 A | 5/1998 |
| GB | 2425488 A | 1/2006 |
| WO | WO03077823 A1 | 9/2003 |
| WO | 2005006980 A1 | 1/2005 |

OTHER PUBLICATIONS

Djarova et al., "Human Growth Hormone, Cortisol, and Acid-Base Balance Changes After Hyperventilation and Breath-Holding", Int'l J. Sports Med., vol. 7, No. 6, pp. 311-315, 1986.
Bosco et al., "Hormonal Responses to Whole-Body Vibration in Men", Eur. J. Appl. Physiol. (2000) 81:449-454.

\* cited by examiner

*Primary Examiner* — Clinton T Ostrup
(74) *Attorney, Agent, or Firm* — Barkume & Associates, P.C.

(57) ABSTRACT

A pulsed breathing device has a base unit containing a motor and control circuit and a detachable head unit containing a valve, driven by the motor, which can interrupt the flow of air being breathed.

17 Claims, 17 Drawing Sheets

LEGEND

- 117 mouthpiece
- 118 inlet
- 121 conduit
- 130 rotary valve
- 140 rotary valve
- 131 valve
- 141 valve LEGEND
217 mouthpiece
218 inlet
218a inlet
221 conduit
221a conduit
230 valve
231 motor
240 valve
241 motor LEGEND
100 conduit
101 inlet
102 mouthpiece
103 sensor
104 sensor
105 inlet sensor
106 data processor
107 valve LEGEND
100 conduit
101 inlet
102 mouthpiece
103 sensor
104 sensor
105 inlet sensor
106 data processor
107 valve
108 feedback facility LEGEND
100 conduit
101 inlet
102 mouthpiece
103 sensor
104 sensor
105 inlet sensor
106 data processor
107 valve
108 feedback facility
109 warning device
110 storage device
111 control system
112 cable
113 wireless link

Fig. 17a   Fig. 17b   Fig. 17c
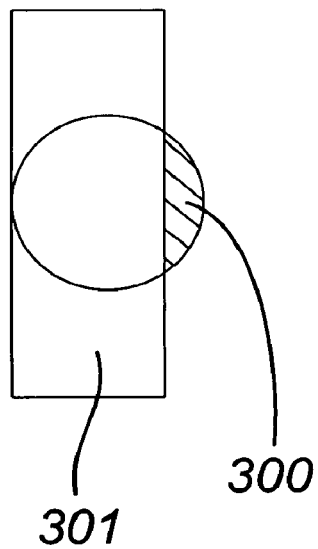
LEGEND
300  plug
301  conduit
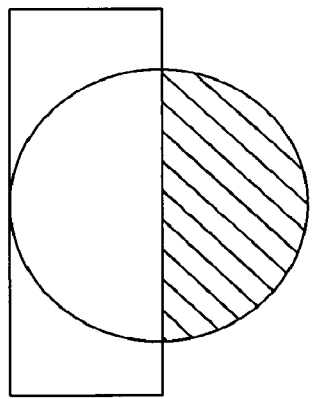
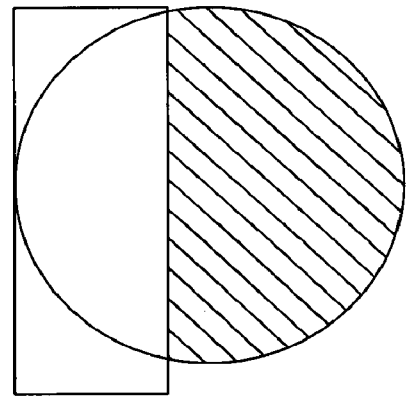

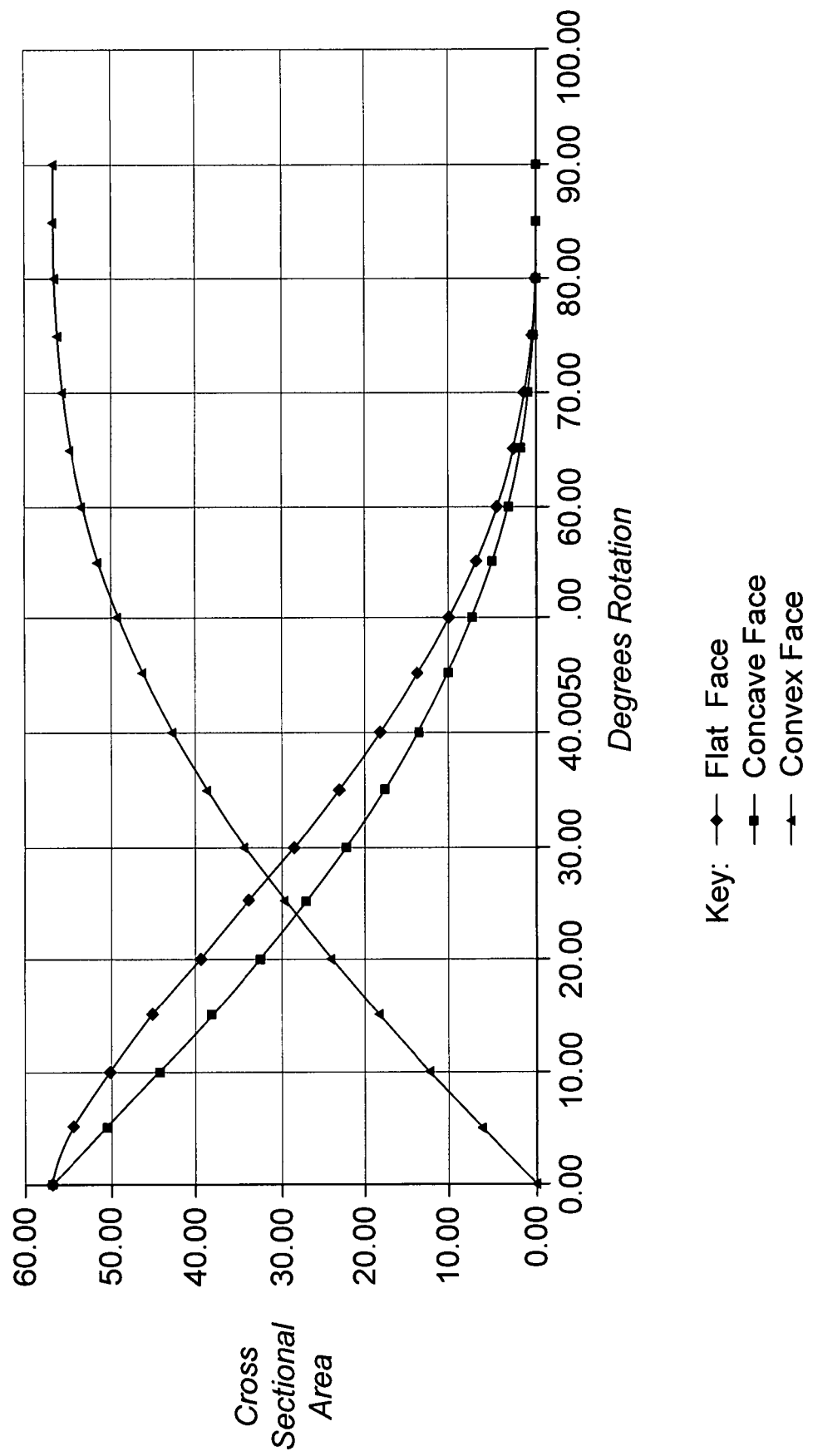
Fig. 18 Valve Cut-Off

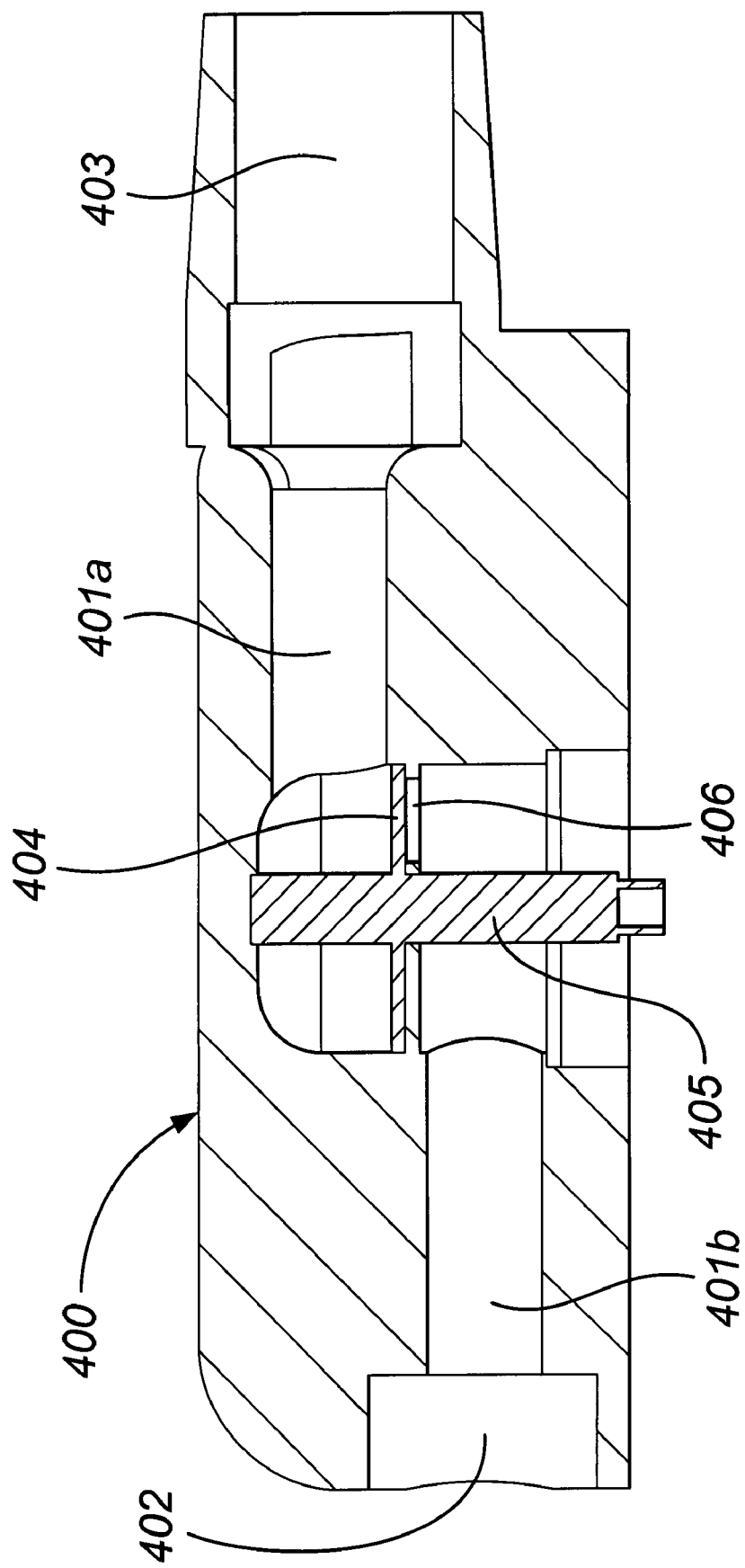

PORTABLE BREATHING DEVICE

CROSS-REFERENCE TO RELATED APPLICATION

This application is related to our co-pending U.S. application Ser. No. 11/845,898, entitled RANDOMLY INTERRUPTED BREATHING DEVICE which was filed on Aug. 28, 2007, the same date as the present application, and which is assigned to the same assignee as the present application.

BACKGROUND OF THE INVENTION

The present invention relates to a portable breathing device for providing resistance and intra-trachea bronchial percussion on breathing in and breathing out to increase pulmonary efficiency while improving cilial movement which assists mobilisation of intrabronchial mucous or secretions within the lung. It can be used for increasing breathing efficiency and for training athletes and also in the treatment of medical conditions related to weak breathing.

Patent Application WO 03/077823 discloses a breathing device having an air flow interruption means connected to the breathing means, which causes a regular periodic interruption to air flowing through the interruption means to the user.

U.S. Pat. No. 6,083,141 discloses a breathing device which incorporates a pair of rotating cylinders which interrupt the flow of air to a user of the device.

These devices will strengthen and develop the muscles associated with breathing as well as assisting in the development of breath capacity in athletes, singers etc.

The devices can also be used for medical applications, for example in the treatment of emphysema, bronchitis, asthma and chronic obstructive pulmonary disease.

However in medical applications when the device is to be used by several people who are suffering from illnesses, particularly infectious illnesses, there is a very real risk of cross infection unless the breathing device is thoroughly sterilised between uses. It is not normally adequate to have a detachable mouthpiece which can be sterilised as the exhaled air and bodily fluids etc. will be trapped in the air passageways. Sterilisation using high temperatures or sterilising solutions can cause problems as the motor and control systems etc. of the device can be adversely affected and they are expensive and difficult to seal effectively.

The present invention provides a breathing device which overcomes these problems and which also possess many other advantages.

SUMMARY OF THE PRESENT INVENTION

According to the invention there is provided a breathing device which comprises:
 a base unit;
 a head unit detachably attached to the base unit;
 a conduit in the head unit one end of which is connected to a mouth piece through which a user can breathe and the other end of which is connected to an air inlet; and
 a valve mounted in the conduit which valve can interrupt the flow of air in the conduit. The mouthpiece can be detachable and can fit over the mouth and/or nose of a user so that a user breathes in through the mouthpiece and this mouthpiece is connected to the valve in the conduit.

There can be a flow restrictor in the air inlet to adjust the flow of air. Preferably the restrictor is removable, whereby removing the restrictor allows a change in the pulse amplitude with respect to background flow resistance. Preferably also the restrictor is variable.

When no flow restrictor part is fitted, a small background flow resistance can be provided by selection of a suitable bore dimension such that, in normal circumstances, a user may start training without a restrictor and still experience some benefit from use, whilst after some use and improvement in user performance or with fitter, more developed users, a restrictor may be fitted to increase the background flow resistance.

The breathing device can provide resistance to both breathing in and out if desired.

The valve can be arranged to produce regular periodic interruptions to the flow of air reaching the mouthpiece being breathed in and out by a user. The frequency of the interruptions to the airflow is controlled by the speed of operation of the valve and is preferably adjustable so that it can be varied for different users or different stages in the use by a single user. There may be a control circuit to control the speed of the valve.

The frequency of the interruptions to the flow of air is preferably in the range of 5 to 100 Hz, for example 10 to 50 Hz, typically 20 Hz. This means that the flow of air through the interruption means is interrupted at this frequency. It has been discovered that the muscles involved in different regions of the respiratory system are strengthened by different interruption frequencies. Typically the diaphragm may be strengthened the more by an interruption cycle of the order of 5 Hz while for upper respiratory areas 20 Hz to 30 Hz may be the more appropriate. Variability in the interruption rate may accordingly be desirable. This can be obtained by interchangeability of the valves or variability of the speed of operation.

Any valve which can interrupt the flow of air down the conduit can be used. For example the valve may be a rotary valve driven by a motor in the base unit. In one embodiment the axle of the motor detachably fits into a slot or in the drive mechanism of the valve or vice versa.

The rotary valve may comprise:
 a housing containing a fluid flow path with a central axis;
 a plug having a sealing face cooperating with a valve seat in said housing in the closed position to block the fluid flow path; and
 a support shaft arranged to carry said plug and being rotatable on an axis which is normal to and spaced from the axis of said valve seat and located outside of the flow path so that rotation of the said shaft moves said plug means relative to said housing.

The axis of the plug need not be outside of the flow path, but preferably neither the bearings nor the remainder of the valve occlude the fluid path. The plug axis may be located at an offset (e.g. to one side) and the offset may be adjusted for different effects. The distance between the axis of the support shaft of the plug and axis of the fluid flow path is herein called "the offset".

When the closed or sealing face of the plug is presented in the bore, flow is totally occluded whilst a 90 degrees rotation of the rotary valve will present a completely open aperture allowing full flow through the valve assembly without obstruction due to the operating mechanism of the valve. The plug preferably has a plane face and, in the open position, this plane is contiguous with the side of the fluid flow path for smooth flow down the fluid flow path.

The plug means is preferably substantially cylindrical or spherical and has a radius larger than the diameter of the flow path; however the cross-section of the plug may deviate from strict circularity.

If the offset and plug diameter are increased while the width of the sealing face of the plug is maintained as equivalent to the bore diameter, a shorter angular opening period is provided for any given rotational speed, which can prove useful if a specific mechanical timing/angular relationship is desired between the valve assembly and the drive mechanism rotating the plug to operate the valve.

A further increase in the plug diameter and its locating bore can provide a closure seat in the flow-bore for even better sealing characteristics due to the overlap of position with a small overlap at the edges of the plug and the housing to ensure good sealing in this position.

By introducing variations in the relationship between the width of the sealing face of the plug, port diameter and valve offset, a variety of different conditions may be created to suit the specific application requirement.

The valve offset, diameter and position provide for good sealing when closed, zero flow occlusion when open, and the ability to use a motor-gearbox speed reduction that is half that which is otherwise required with an on-axis rotary valve.

By presenting the sealing face of the plug in the flow path once in each revolution motor speeds are doubled for any given flow pulse rate when compared to conventional on-axis designs which close the valve twice in each revolution; this causes less low-speed motor torque problems.

Another type of valve comprises a solenoid driven diaphragm placed in the air flow path. In this case the motor means is a solenoid which may be operated by an electronic pulse and the diaphragm may be retained in a detachable head Yet another type of valve is a diaphragm or mechanical port which may be opened and closed by action of motor means in the form of a piezo actuator device which is operated by an electronic pulse.

Usually the motor means is a rotary motor powered by a battery, which may be a rechargeable battery. Mains power may alternatively be used. The motor means may in another embodiment be a hand driven clockwork motor, or a hand drive may be incorporated to charge a battery for a battery driven motor. In yet another embodiment the motor means is a breath driven rotary vane, the vane carrying a magnet which, in co-operation with a static magnet mounted in the device, provides the valve by virtue of the user breathing alternately with and against the magnetic attraction of the two magnets. Any of these three devices may be constructed as integral units, that is to say without a detachable head.

Yet another type of valve comprises two discs, at least one of which can be rotated relative to the other, with each of the discs having at least one hole in it, the discs being positioned in the air flow so that, as at least one of the discs rotates relative to the other disc; the holes in the two discs are periodically coincident so as to form a continuous air flow passage.

The head unit of the device can be removed and can be sterilised without the sterilisation of the base unit containing the motor and controls. This is of great benefit in hospitals as the sterilisation may need to be carried out using high pressure steam in an autoclave or using reactive liquids which could otherwise affect the motor and its control systems.

A further advantage of the device of the invention is that it enables different head units to be used for different patients and for different applications so that different size conduits, valve speeds etc. can be used without the expense of having to provide a different base unit for each use.

The device of the invention enables specialised heads incorporating data monitoring and data gathering sensors to be used. These sensors can measure pressures, flow rates, adjustment to changes in rate of interruption of the flow etc. The data can be displayed on a display screen on the base unit or stored electronically, e.g. in a chip, which can be removed or downloaded later or the data can be transmitted by a suitable connection to a computer or sent to a remote location for analysis; this can provide a permanent record of a patient's progress, condition etc.

In this way it is possible for a patient's progress to be monitored over a period of time. For example the patient can use the device on a regular basis and at longer intervals of time; the specialised head can replace the regular head and the patient's progress monitored, thus one specialised head can be used to monitor a large number of patients over the same period of time. In existing devices, when the head is not detachable, the provision for use of such expensive equipment on a regular basis would be prohibitively expensive.

It has been observed that users can become accustomed to regular interruption of their breathing, and that this accustomisation can impede further improvement. Accordingly the frequency of operation of the valve may be arranged to vary, possibly randomly. A software or firmware program or electronic hardware circuit may be incorporated to accomplish this. This feature may be particularly useful for sportspersons and sports animals.

One way of accomplishing a varying valve operation is to employ two or more motors, each driving its own valve. These may be in series or parallel. One valve may be at a constant speed and the other varying or both may vary at different rates. Holding one frequency constant, by for example using a fixed DC drive voltage, and sweeping a second motor control voltage gives a pulse sequence with a huge range of harmonics.

Forcible and prolonged inspiration and expiration causes a greater expansion and collapse of the air vesicles (alveoli), especially those deep in the lung tissue. By providing resistance to inspiration and expiration, pulmonary muscles are strengthened and developed, thereby allowing a freer and greater exchange of oxygen and carbon dioxide. Persons suffering from lung ailments, healthy persons, and athletes can all improve their pulmonary efficiency through forcible and prolonged inspiration and expiration against resistance.

The device of the invention will strengthen and develop the muscles associated with breathing and, as well as assisting in the development of breath capacity in athletes, singers etc., it can be used to help develop increased breathing capacity in people who have reduced or defective capacity.

It is a particular advantage of devices according to the present invention that they can be quite compact, enabling relatively unobtrusive one-handed portability, where such portability is desired. In one example the device has a height of 10 cm, a breadth of under 8 cm and a thickness of under 5 cm. This is particularly useful for athletes and even sports animals, but as it has also been realized that, by virtue also of vibration of the device, use of the device can inhibit deep vein thrombosis, and accordingly light weight and very small bulk are particularly advantageous.

Studies have demonstrated that vibration stimulation and breathing manoeuvres can give a five-fold increase in generalised neuroendocrine response (Djarova et al 1986 and Bosco et al 2000). Devices in accordance with the present invention will cause a change in the release of hormones cortisol and growth hormone and accordingly result performance gains in strength, sprint and power.

BRIEF DESCRIPTION OF THE DRAWINGS

Various embodiments of a breathing device in accordance with the invention will now be described by way of example with reference to the accompanying drawings in which:

FIGS. 17a, 17b, 17c illustrate valve plugs with differing chords;
FIG. 18 is a graph of the effects of varying the form of the face of the valve plug;
FIG. 19 is a schematic side section of an alternative head.

DESCRIPTION OF SPECIFIC EMBODIMENTS

Figure 1:
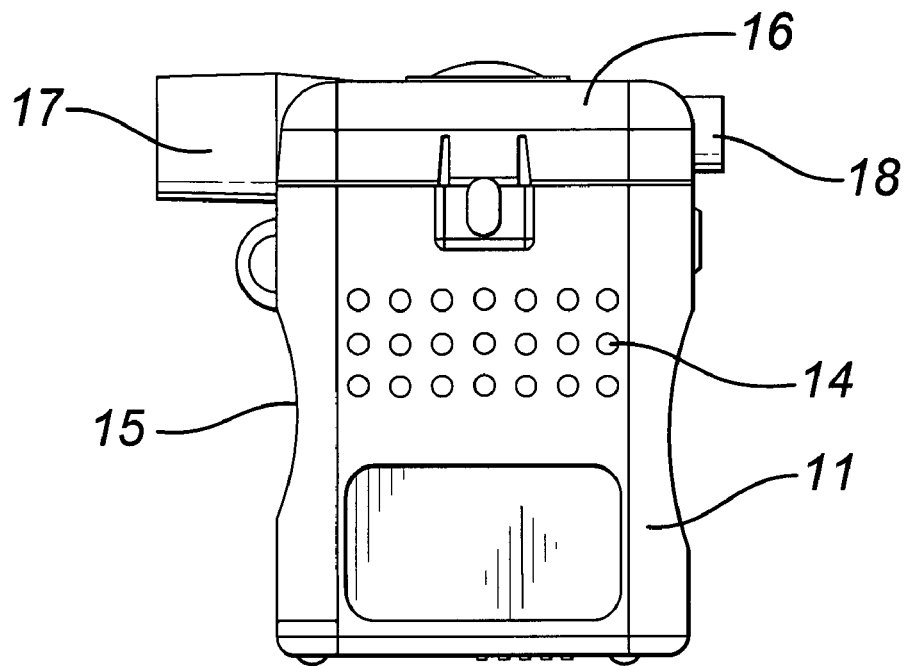
FIG. 1 is a side view of the device.
Figure 2:
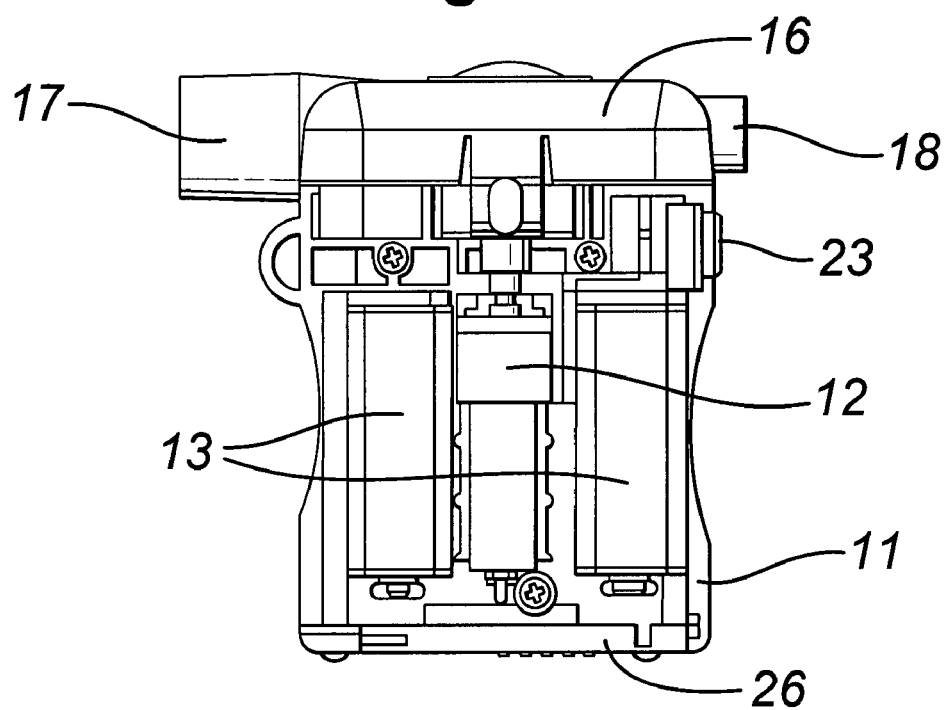
FIG. 2 is a side view of the device with a side panel removed.
Figure 3:
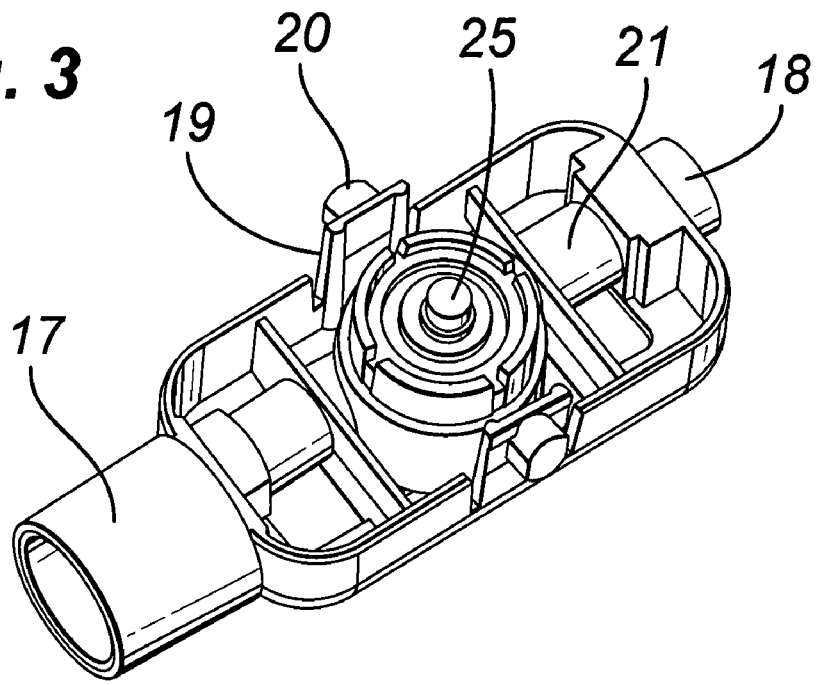
FIG. 3 is an underside ¾ view of the head.
Figure 4:
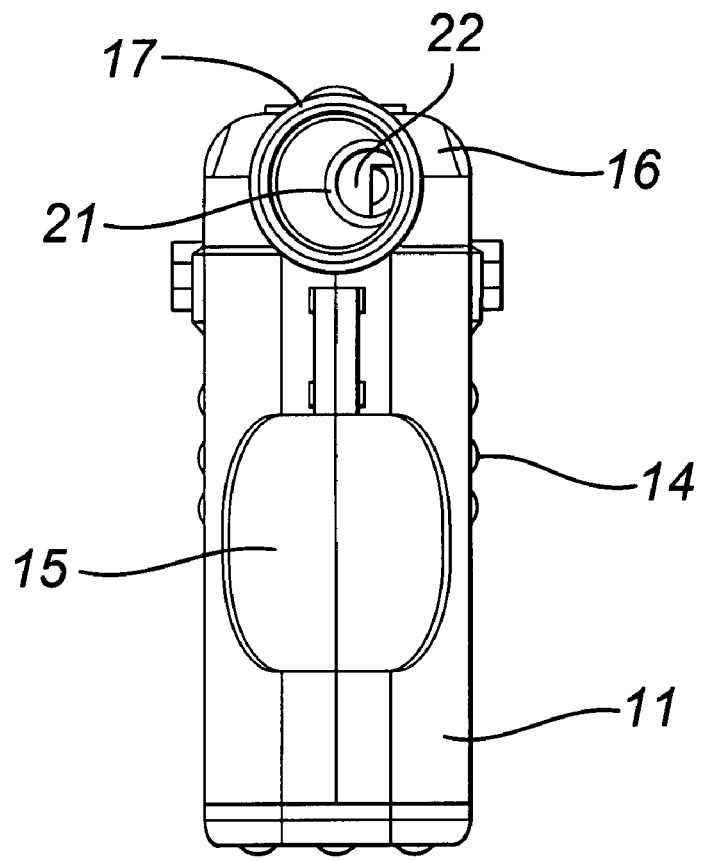
FIG. 4 is a view of the mouthpiece end of the device.

Referring to the FIGS. 1 to 11, the device comprises a base unit 11 containing an electric motor 12 and batteries 13 which drive the motor and associated control mechanisms which enable the speed of the motor to be varied. There are, on the outer surface of the base unit 11 protrusions 14 and an indentation or patterned textured surface 15 which assist in gripping the base unit 11.

Detachably attached to the base unit 11 is a head unit 16 having a mouthpiece 17 and an inlet 18 through which a user can breathe. The detachable attachability is obtained via slots and detents 11a in the base unit 11 into which flexible flaps 19 carrying lugs 20 in the head unit snap fit. The mouthpiece 17 and inlet 18 are linked by a conduit 21 in which there is a rotary valve 22.

The motor is controlled by a control button 23 and drives the valve 22 via a separable motor shaft drive dog 24 and a drive shaft 25. The batteries in the base unit can be accessed through door 26 at the base of the base unit 11.

Figure 5:
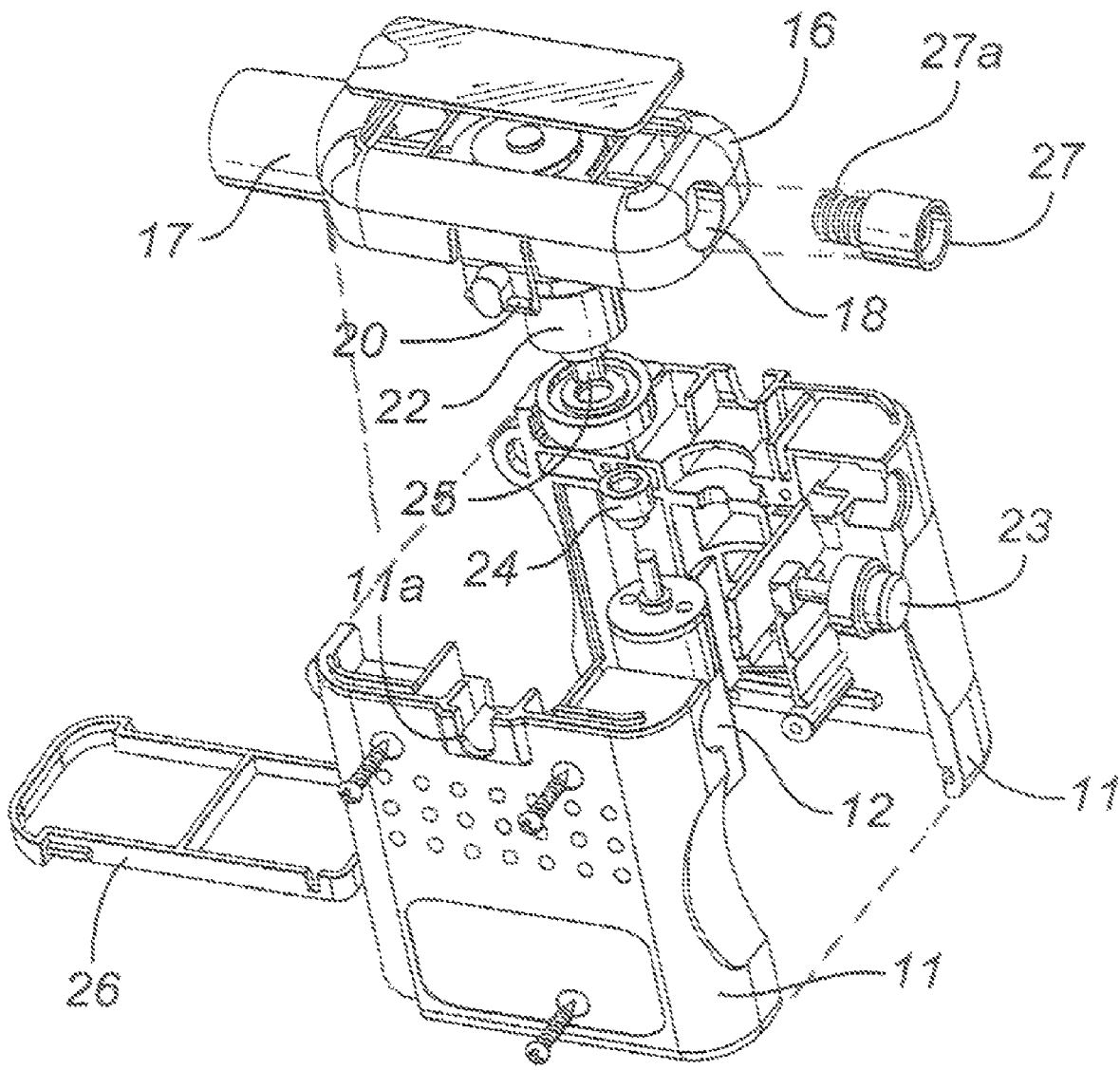
FIG. 5 is an exploded ¾ view of the device.
Figure 6:
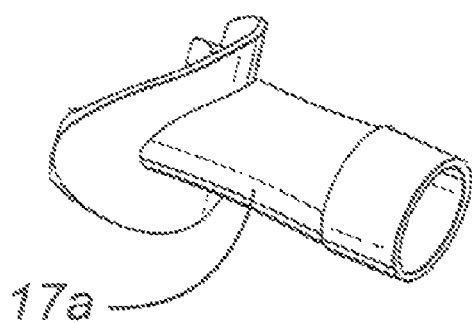
FIG. 6 shows a replaceable mouthpiece.
Figure 7:
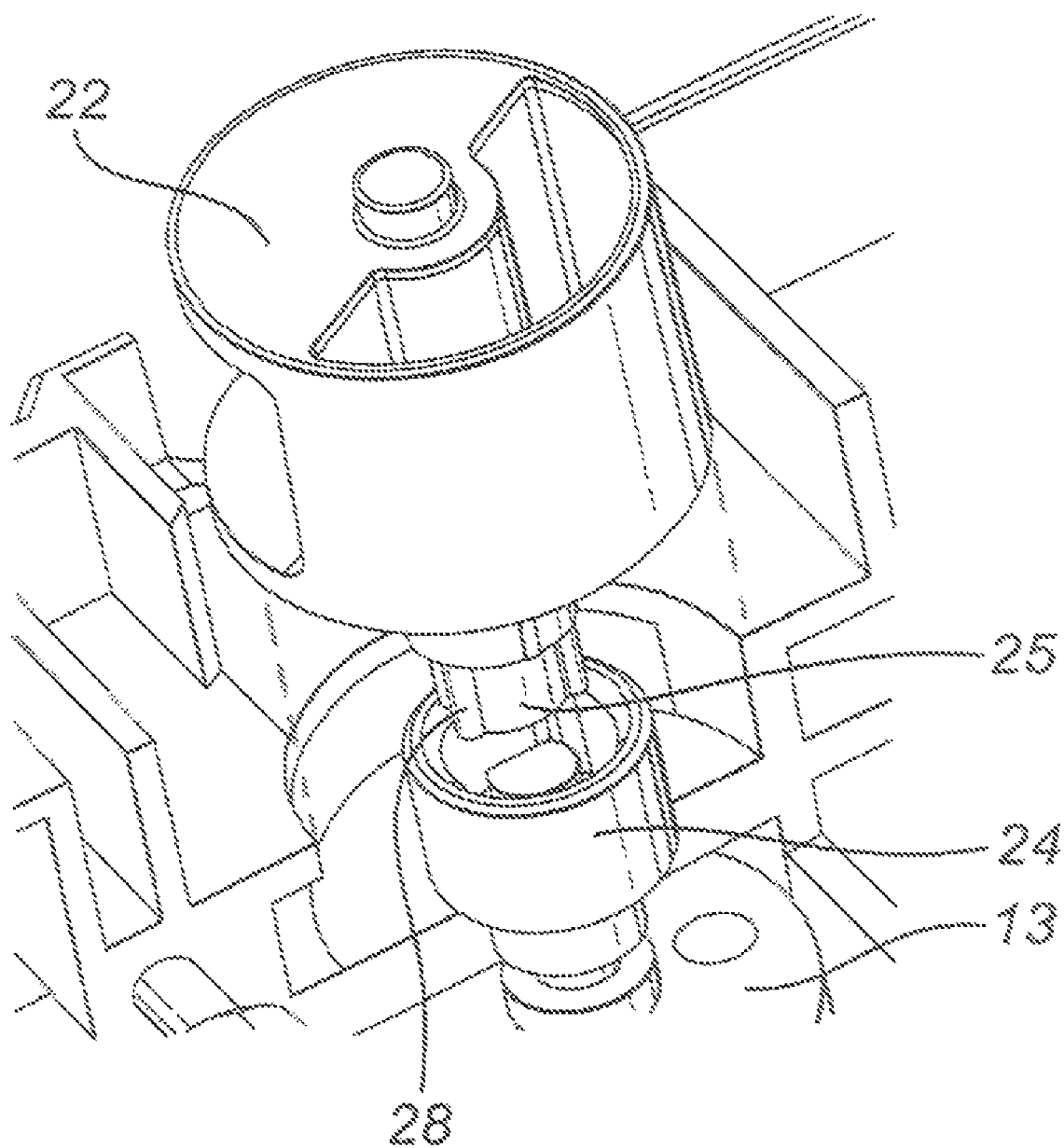
FIG. 7 is an exploded part view of the device showing the valve and motor drive mechanism.

Referring to FIG. 5 there is a restrictor 27 incorporating a deformable tubular section 27a which allows it to be push-fitted into, and retained by, the inlet 18. A variety of different internal bore sizes can be used for the restrictor 27 to produce a variety of different background flow resistances; removing the restrictor 27 allows a change in the pulse amplitude with respect to background flow resistance. In similar manner, as shewn in FIG. 6, a disposable mouthpiece 17a may be push fitted over the mouth stub of the valve head to provide a better seal to the user's mouth and to improve hygiene through being washed or autoclaved at high temperature or discarded and replaced by another unit.

The drive shaft 25 incorporates several narrow radial lands 28 projecting outwards while the drive dog 24, which is mounted on a motor shaft, is provided with a hollow tubular part with a similar number of inward facing lobes. The drive shaft 25 is devised to fit inside the drive dog when the valve head 16 is assembled onto the motor drive unit (base unit 11). The radial lands 28 of the drive shaft are dimensioned so that, as the motor rotates the drive dog, the internal lobes of the drive dog push against the side faces of the projecting lands of the drive shaft and impart radial motion. By provision of a large radial angular gap between the lobes of the drive dog and use of narrow radial lands on the drive shaft and also provision of tapered guide profiles, when inserting the valve head on the motor unit there is only a small chance of the drive shaft lands aligning directly with the internal lobes of the drive dog—preventing easy insertion. In event of this alignment occurring, the tapered profiles of the land and lobe leading edges guide the valve drive shaft (as this rotates more freely than the motor shaft and drive dog) and angular pressure causes it to rotate until the drive dog lobes are presented to a gap between drive shaft lobes, facilitating easy insertion and attachment of the valve head every time this is fitted.

Figure 8:
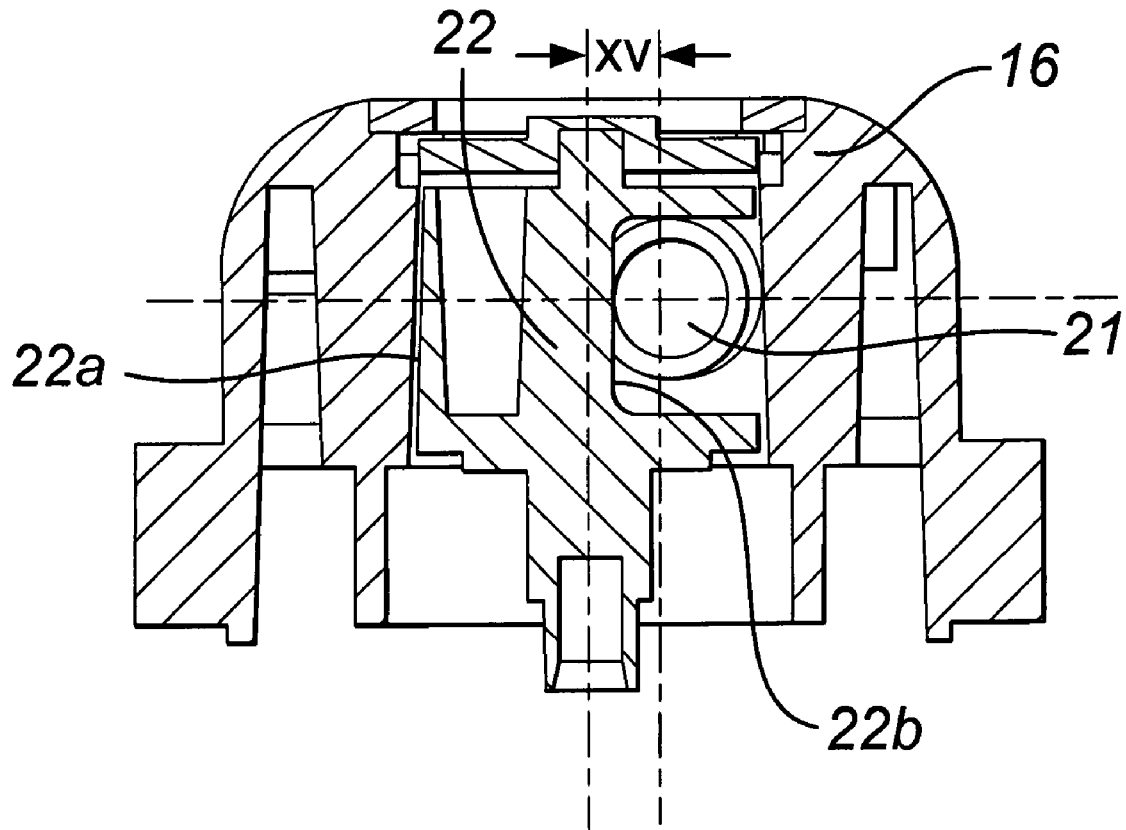
FIG. 8 is a cross sectional view of the valve head showing the valve location and axis offset.
Figure 9:
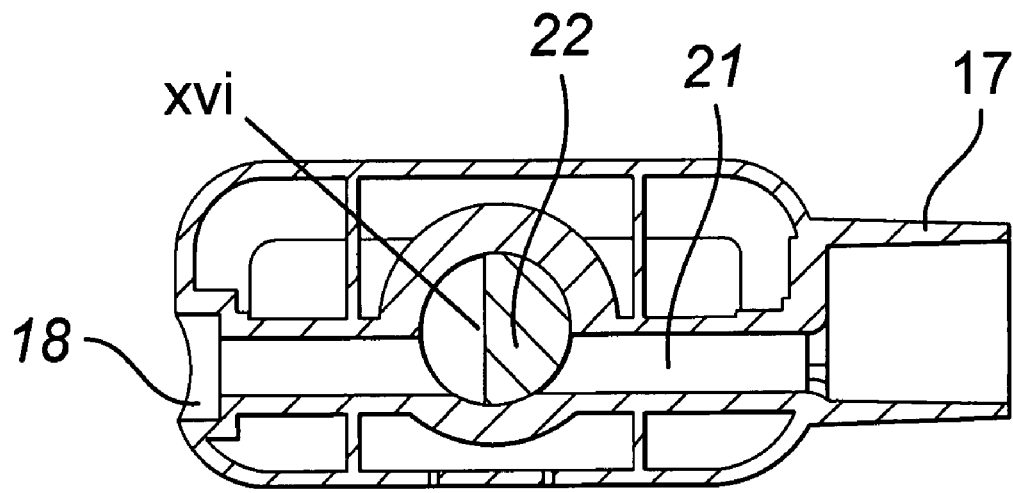
FIG. 9 is a horizontal section of the valve head with the valve oriented in the closed configuration.
Figure 10:
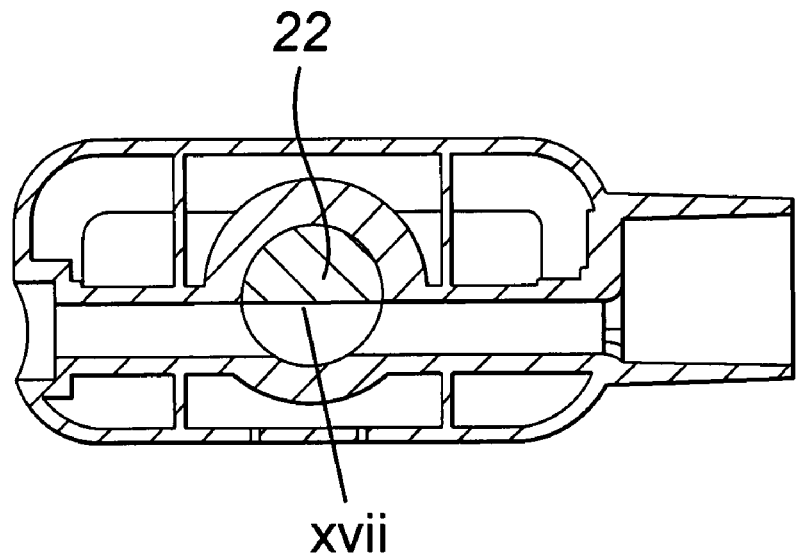
FIG. 10 is a horizontal section of the valve head showing the valve in the open configuration.
Figure 11:
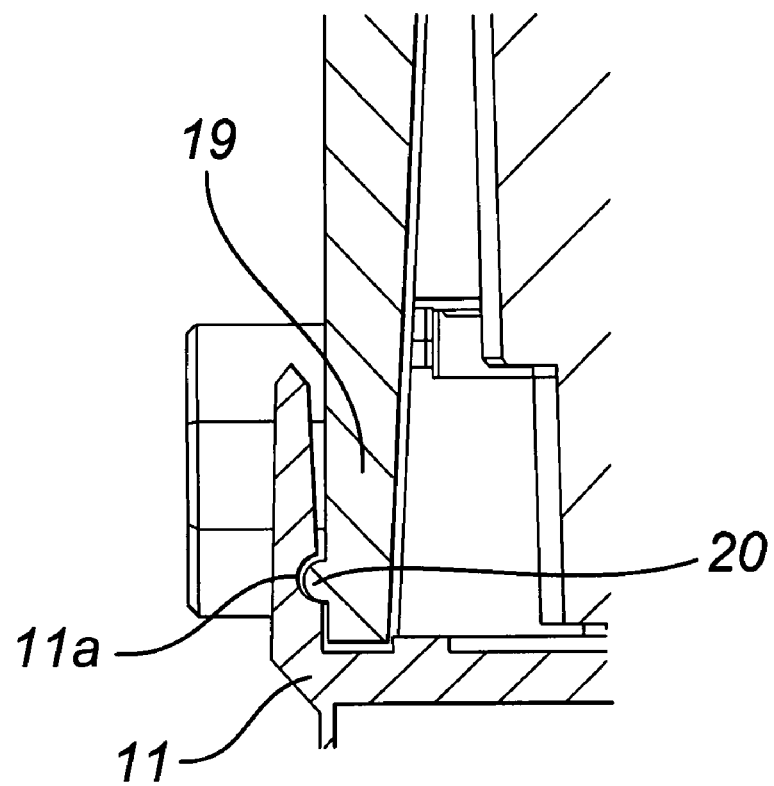
FIG. 11 shows detail of the head to base unit detachable attachment.

The rotary valve 22 is shewn in greater detail in FIGS. 8 to 10. As can be seen the valve 22 is located at an offset (xv) from the conduit 21 main axis and has a solid closing face 22a and a cutaway face 22b.

Referring to FIG. 9 when the rotary valve 22 is oriented in the shown position (xvi) it occludes the conduit 21 and thus provides a closure to the fluid flow. The valve rotates at approx 10 Hz to 100 Hz and thus provides a changing resistance to fluid flow with a maximum resistance occurring when the valve is in the shown fully closed position against which the user breathes. During inhalation if the valve is in this position a partial vacuum or lowering of pressure will occur between the user and the valve, while during exhalation a positive or excess pressure will occur in the conduit between the user and the valve. In intermediate valve rotation positions there will be essentially sinusoidal variations in developed pressures.

Referring to FIG. 10 when the valve 22 is oriented in the shown position (xvii) it allows free flow of fluid in the conduit.

In use the head 16 is attached to base unit 11 so that drive shaft 25 fits into and is driven by the drive dog 24 mounted on the motor shaft of the motor in the base unit. The lugs 20 snap fit into the slots thus holding the head unit in place. A user presses button 23 which starts the motor in the base unit so that the rotary valve in the head unit rotates opening and closing the valve and interrupting the flow of air in conduit 21. The user breathes in through mouthpiece 17 and air enters at the inlet 18 via restrictor 27 and passes along the conduit 21 where the flow is interrupted by the valve 22 so that the flow of air into the user's lungs is interrupted; the user can then breathe out through the valve 22 and the outlet and restrictor 27. The speed of rotation of the motor can be varied during manufacture, which varies the frequency of the valve opening and closing and the flow of air to and from the user; this is set for optimal performance enhancement as dictated by experimental result, but is envisaged as between 5 Hz and 100 Hz and usually between 10 Hz and 50 Hz.

When the device is to be used by another user the head 16 can be removed and sterilised. Alternatively each patient can have their own head unit so that several patients can have a personal head unit for their own use with one base unit used for all the patients.

It is noteworthy that the portable device described has the following dimensions: height 10 cm, breadth 75 cm or 95 cm, thickness 44 cm. Its weight is less than 200 g. It is consequently susceptible of being comfortably held in one hand. Alternatively it can readily be mounted on a harness worn on the user's head.

Figure 12:
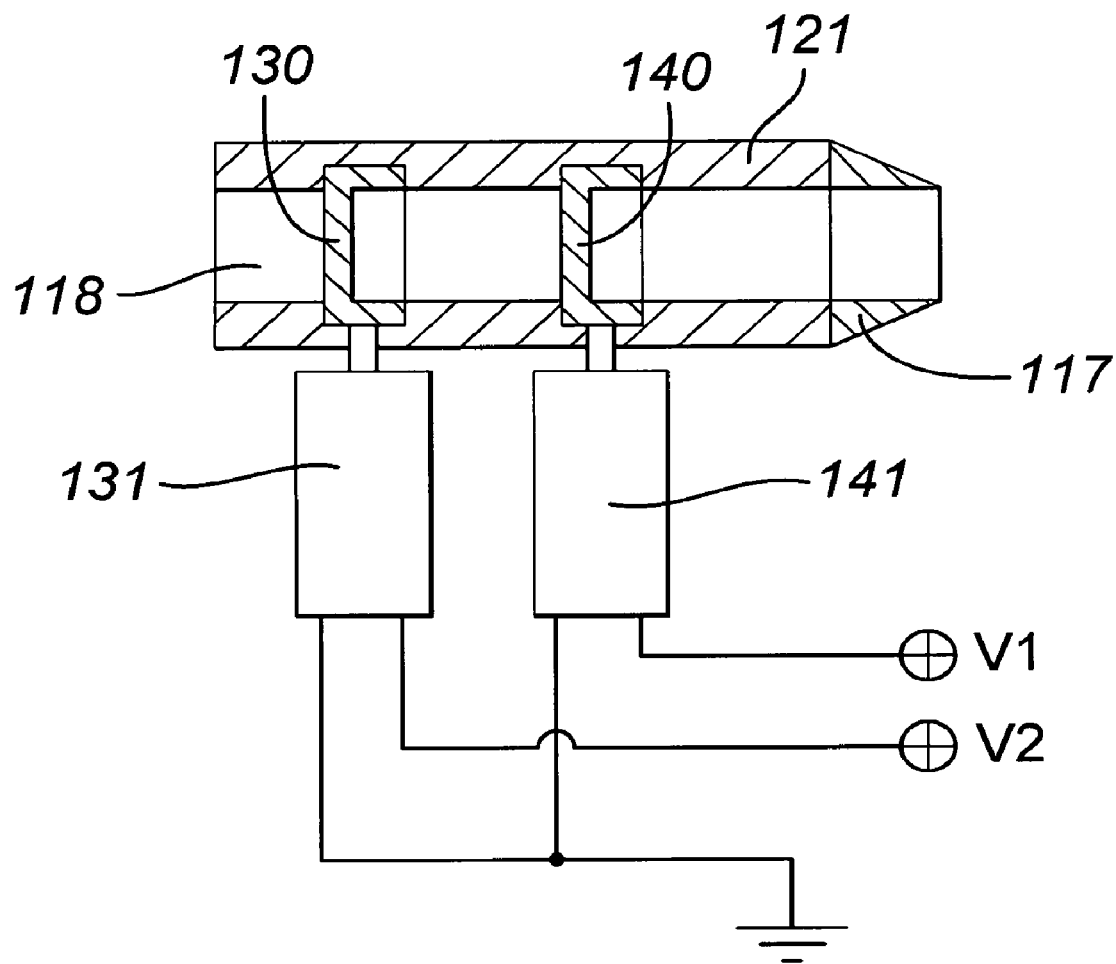
FIG. 12 is a schematic part view of a double motor device with valves in series.

The alternative embodiment illustrated in FIG. 12 has a mouthpiece 117 and an inlet 118 linked by a conduit 121. Across the conduit are two rotary valves 130, 140 in series. The valves are driven by motors 131, 141 respectively. The motor 131 is arranged to operate at constant speed while the motor 141 is arranged to operate at a constantly varying speed. The valves 131, 141 are constructed to occlude airflow for a very small arc of their rotation to arrive at an acceptable base flow occlusion. By this arrangement a considerable variation of occlusion rate is obtained.

Figure 13:
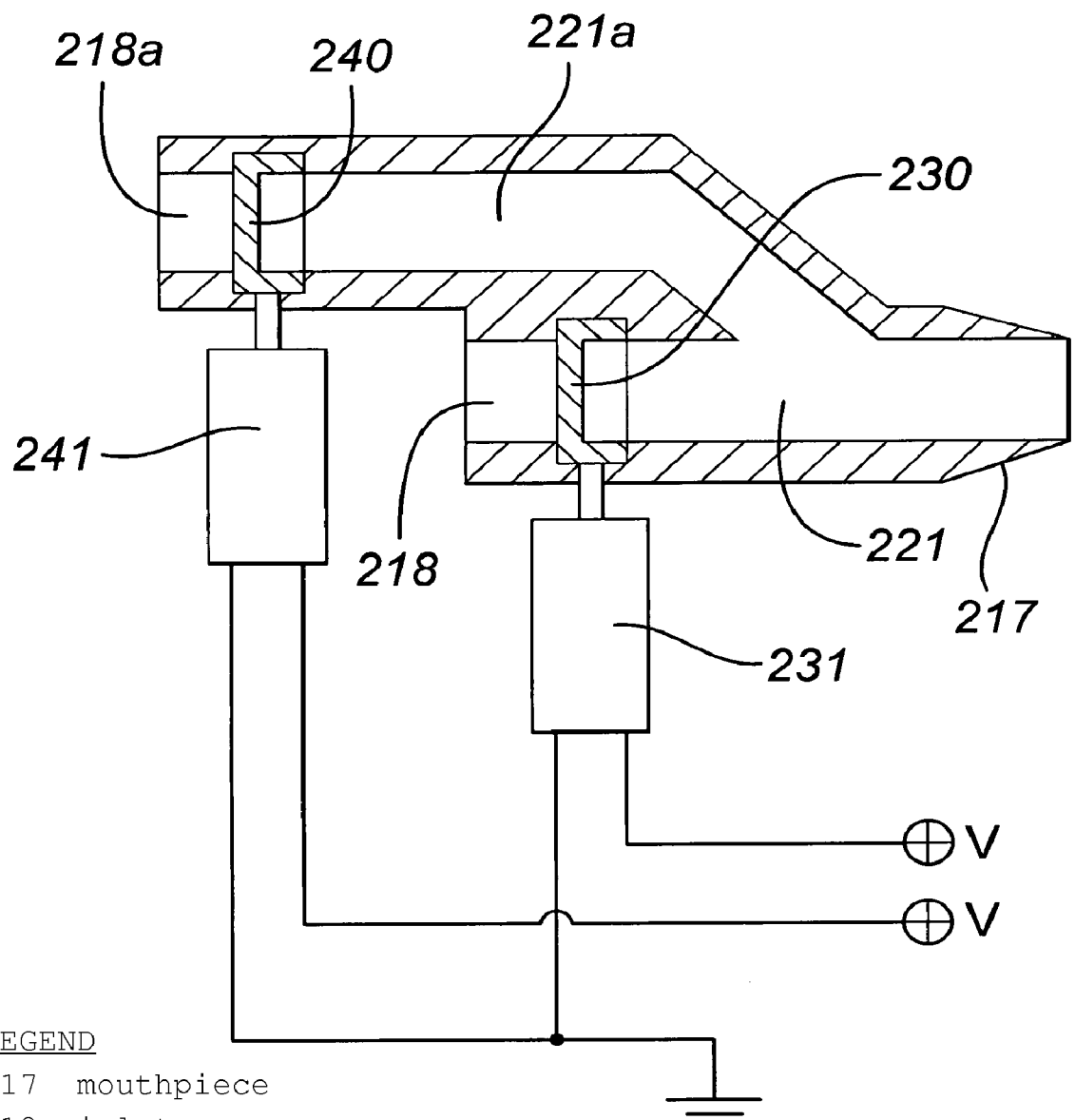
FIG. 13 is a schematic part view of a double motor device with valves in parallel.

The alternative embodiment illustrated in FIG. 13 has a mouthpiece 217 with two associated inlets 218, 218a linked by parallel conduits 221, 221a. Across each conduit 221, 221a is a valve 230, 240 driven by motors 231, 241 respectively. The motor 231 is arranged to operate at constant speed while the motor 241 is arranged to operate at a constantly varying speed.

The motors 131, 141, 231, 241 are conventional DC brush motors and gearboxes permit the valves to rotate at speeds considerably lower than the motors. Stepper motors could be employed instead.

Figure 14:
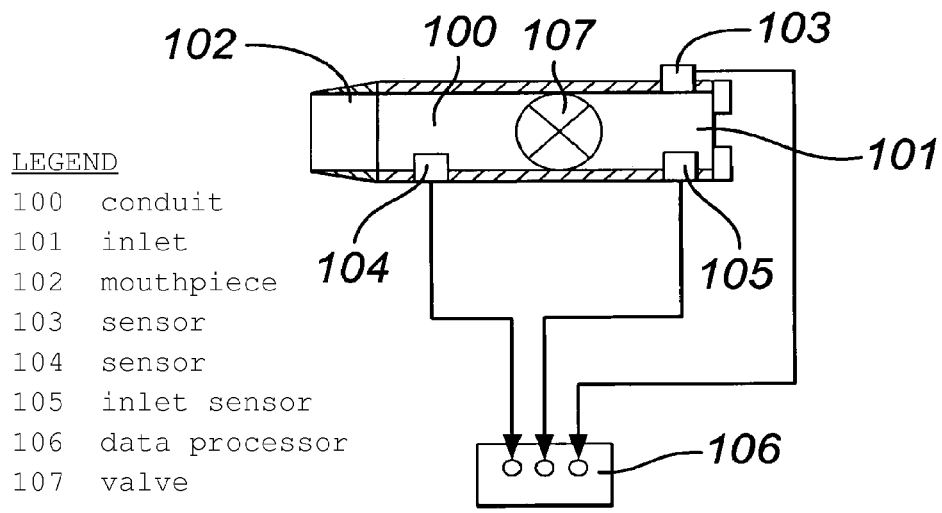
FIG. 14 is a block diagram of a basic monitoring sensor facility.

When data about a user's performance is to be monitored, a head unit containing the appropriate sensors can be used instead of that described above. A simple such head unit is illustrated in FIG. 14 which shows a detachable head unit conduit 100 having an inlet 101, a mouthpiece 102 and a valve 107. These correspond to the conduit 21, mouthpiece 17, inlet 18 and valve 22 described above with reference to FIGS. 1 to 11. Exterior to the conduit is an ambient sensor 103 of temperature and pressure. Inside the conduit 100, inboard of the mouthpiece 102, is a "user side" sensor 104 of temperature and pressure. Inside the conduit 100, just inboard of the inlet 101, is an inlet sensor 105 of temperature and pressure. The three sensors are connected to a data processor 106.

Figure 15:
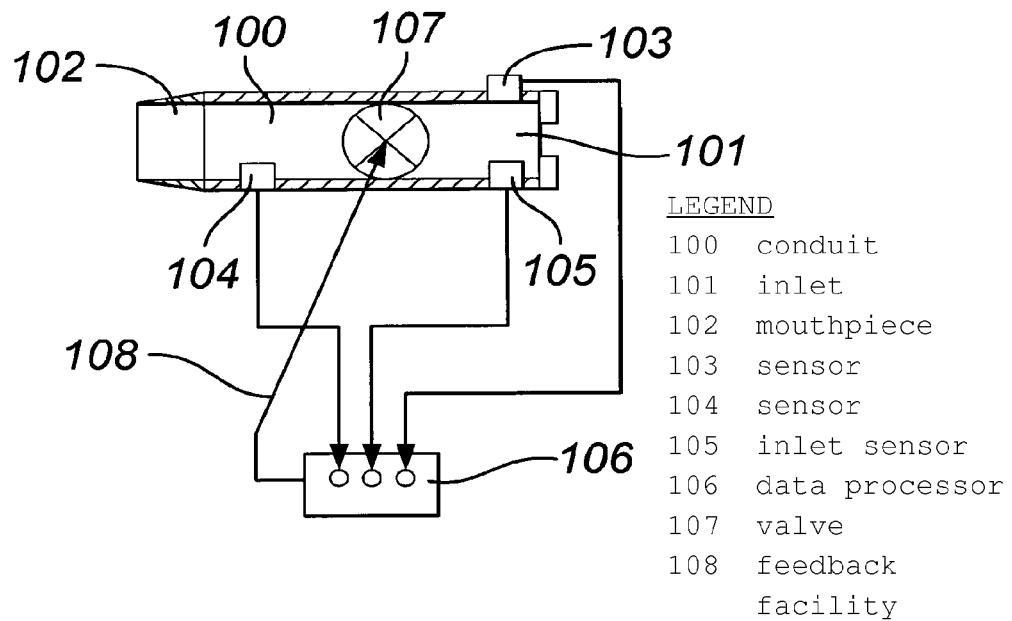
FIG. 15 is a block diagram of a monitoring sensor facility incorporating feedback.
Figure 16:
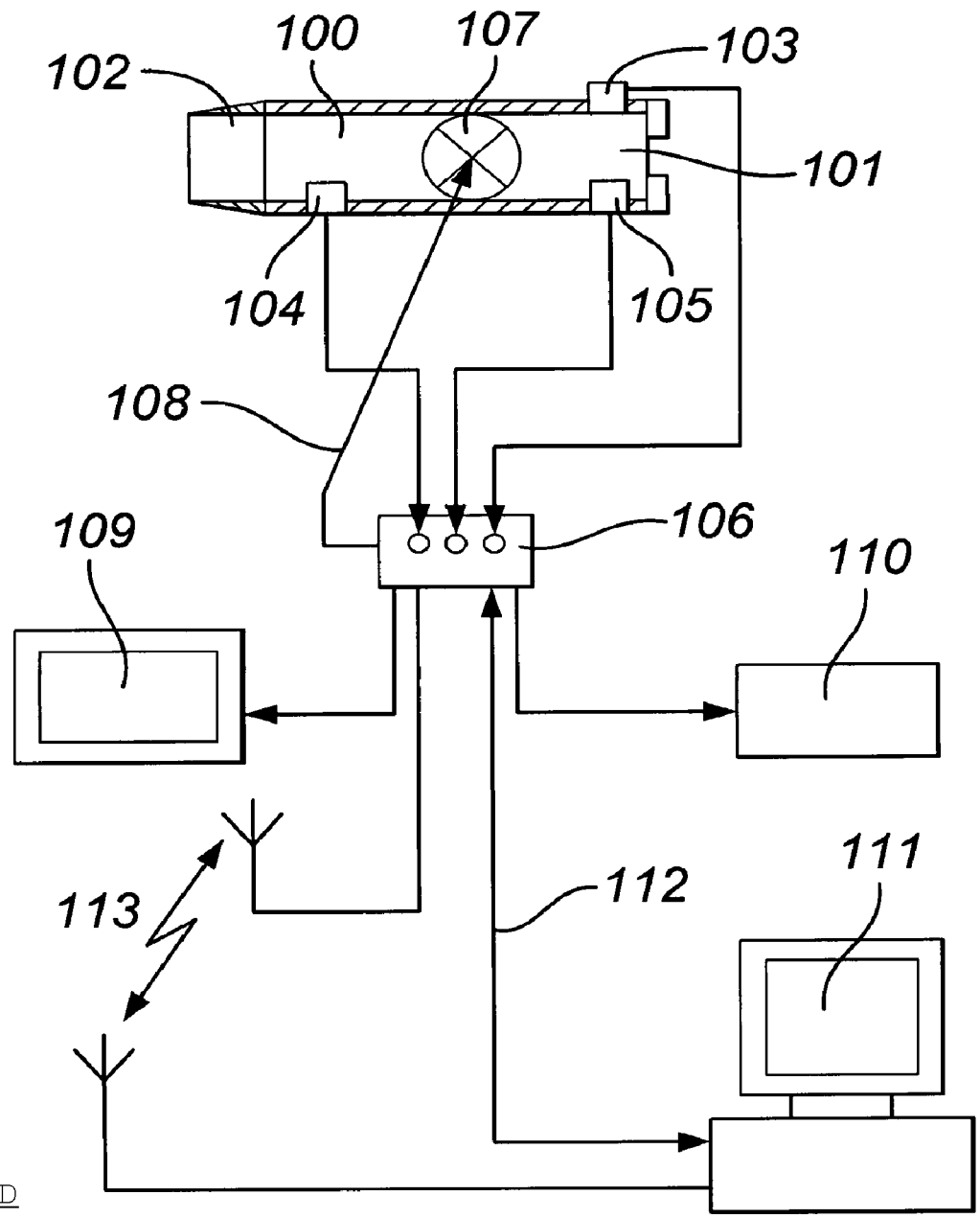
FIG. 16 is a block diagram of a complete monitoring facility.

FIG. 15 illustrates a head unit such as that described above with reference to FIG. 14 but incorporating a feedback facility 108, FIG. 16 illustrates a number of different ways in which output from the data processor 106 can be utilised. An on-board display or warning device 109 provides real time performance information to the user, his medical adviser or his trainer. An on-board data storage device 110 stores performance data for recordal and subsequent analysis. A remote data storage, processing, viewing management and control system 111 is associated with the data processor 106 either via cable 112 or wireless (radio, infra-red, blue tooth) link 113.

The sensors 103, 104, and 105 and the data processor 106 are actually mounted in the base unit 11 and the sensors 104 and 105 protrude into the conduit 100 when the head unit 16 is mounted to the base.

FIGS. 17a, 17b, 17c illustrate schematically valve plugs with different degrees of "cut-away". In FIG. 17a, most of the valve is "cut away" and the axis of rotation of the plug 300 lies within the boundaries of the conduit 301. This construction is produced by having a base to the plug, not shewn, disposed beneath the conduit and associated with a drive shaft. Its effect is to produce a large valve opening time in relation to closed time, per revolution. In FIG. 17b the plug axis is tangential to the conduit boundary, approximately half the cylinder forming the valve is "cut away" and valve open and closed times per revolution are approximately equal. In figure 17c the plug axis is outside the conduit and less than half the cylinder forming the valve is "cut away". In this case during each revolution the valve is closed for longer than it is open.

Of course the face of the valve does not have to be planar and some modification of the airflow waveform can be obtained by varying it. FIG. 18 compares the effects of a face which is somewhat concave or somewhat convex compared to one which is planar. The planar face valve defines a flow variation which is substantially sinusoidal. A concave face generates a shallower rate of area presentation while a concave face will cause an earlier start to the cut-off and a gentler rate of opening near to maximum.

Figure 20:
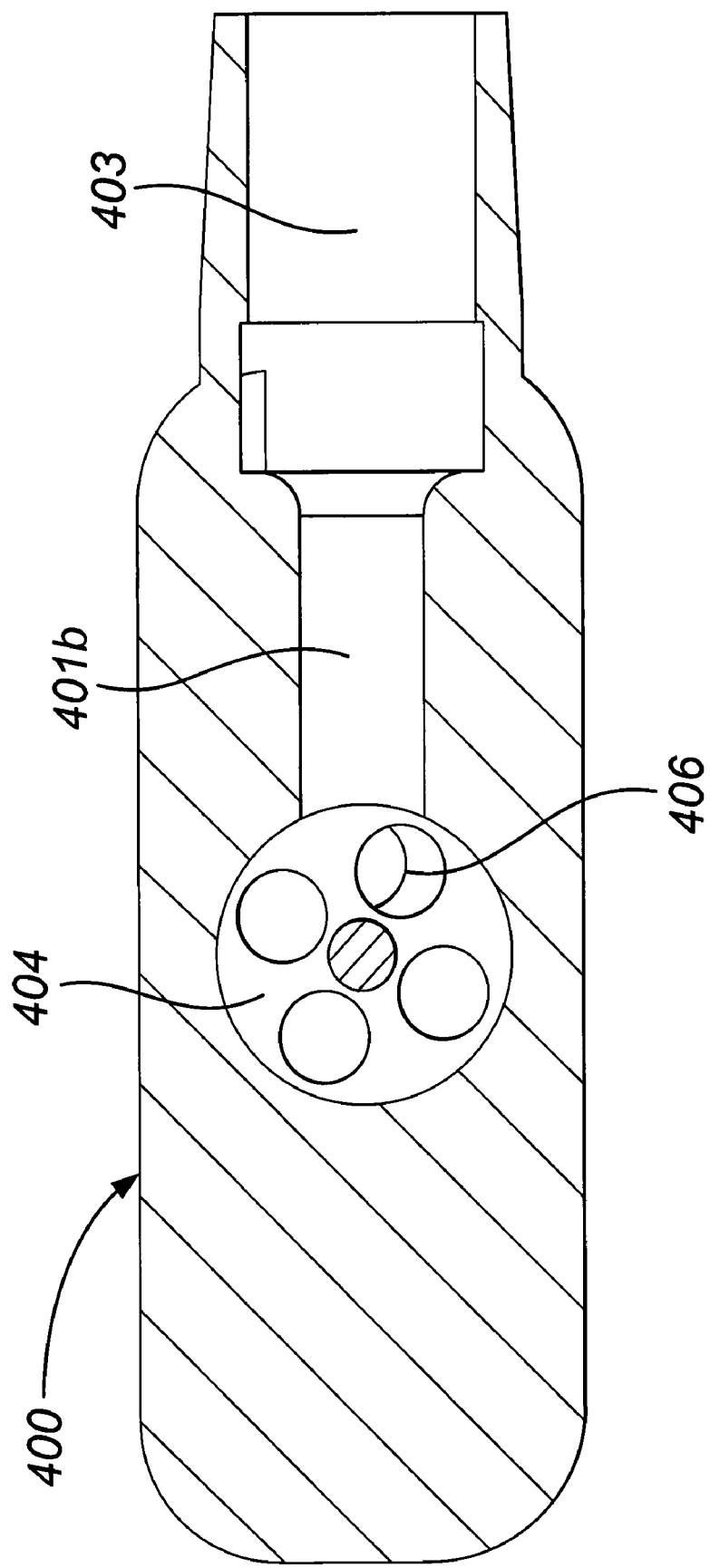
FIG. 20 is a schematic plan section of the alternative head illustrated in FIG. 19.

Another embodiment of the head of the device, a disc valve version, is illustrated in FIGS. 19 and 20. The head 400 defines a conduit in two parts 401a, 401b having an inlet 402 and a mouthpiece 403. The axes of the two parts of the conduit are offset and parallel. Between them is sited a disc valve 404 mounted on a drive shaft 405 and a co-operating valve base plate 406. As shewn the valve 404 and the base plate 406 are foraminous. However a variety of forms of perforation of the valve 404 and the plate 406 are possible. Where a slow enough motor or minimal or nil gearing are possible in the production of effective breathing checks, the disc and the plate may each be simply cut away to provide one check per revolution. Different shapes of the cut away and the holes (or slots) will vary the airflow wave form. Moreover, an irregular spacing of foramens around the disc provides a degree of randomness to the intermittence of the airflow cycle.

If desired the device head may be arranged so that discs can be interchangeable.

Alternative embodiments of the invention incorporate an adjustable speed control. In one of these this adjustment is arranged for control by the user; in another, once initiated it is arranged for periodic speed variation and in another for random speed variation. These facilities are particularly valuable in training athletes and animals used in sport. The sensors 103, 104, 105 may also detect relative humidity.

Normally in the hand-held device envisaged the power to drive the motor is from a battery incorporated in the base of the device, which may be rechargeable. Mains power may alternatively be employed. In another alternative a power storage unit is employed whence the electricity is derived by turning a handle manually.

Figure 21:
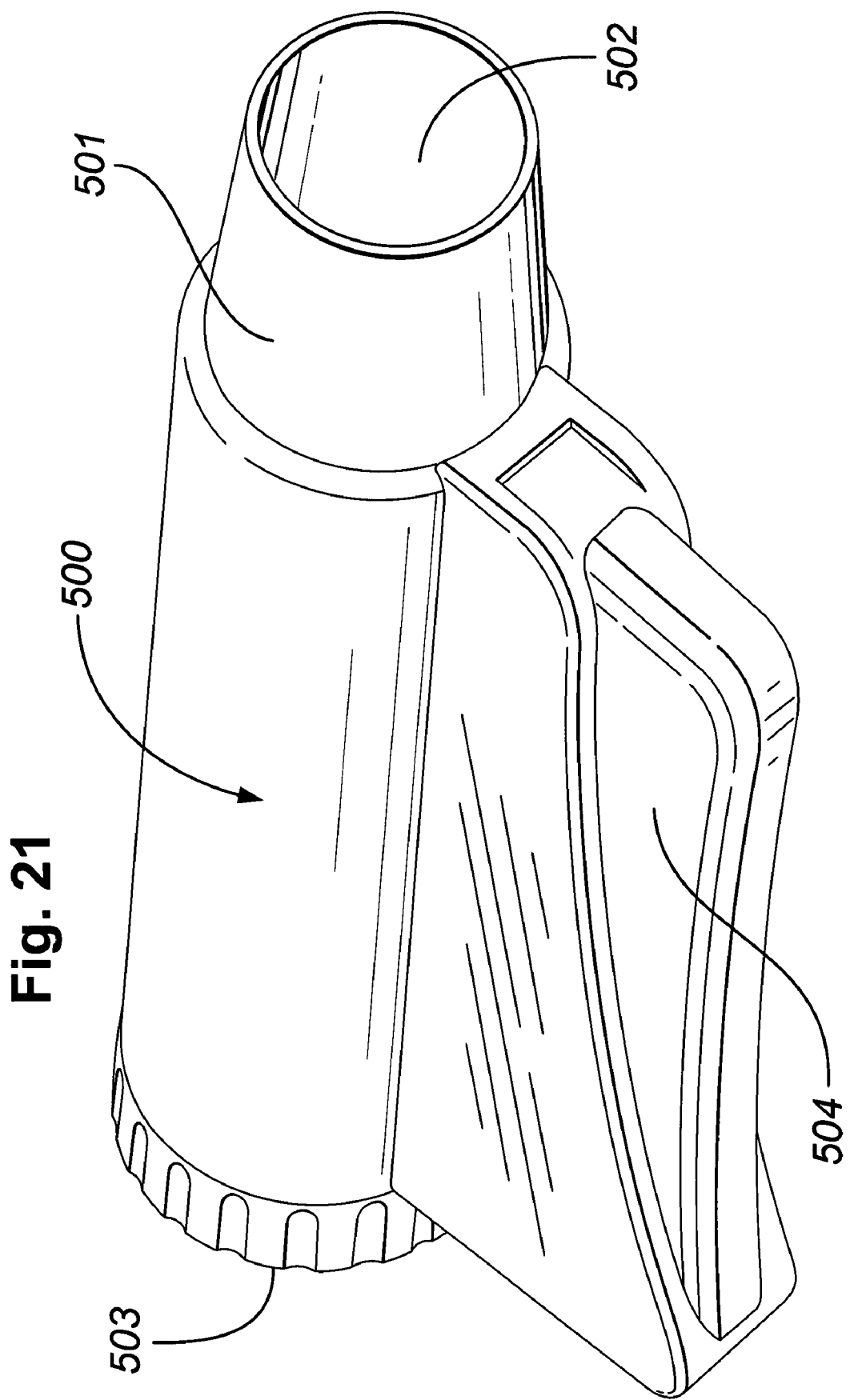
FIG. 21 illustrates manually operable device.

The device illustrated in FIG. 21 comprises a housing 500 incorporating a mouthpiece 501 to a conduit 502 and an inlet 503. A hand squeeze lever 504 is associated with a one-way drive mechanism plus flywheel and gearing (not shewn). The lever 504 has radial gear teeth near a pivot end thereof, which teeth engage with a gear on a shaft through a pawl and ratchet or other one-way drive mechanism. A roughly 30 degree angular movement caused by squeezing the lever 504 rotates the shaft about four times. Via the gearing the flywheel is rotated ten times for each shaft rotation and this gives a reasonably steady speed. The flywheel is associated with a valve which may be of the plug or disc type as described above. The device illustrated may have a detachable head, or the detachable head may simply comprise the mouthpiece. Given that the device is personal and does not necessarily contain parts deleteriously affected by repeated sterilisation a detachable head may not be needed.

Figure 22:
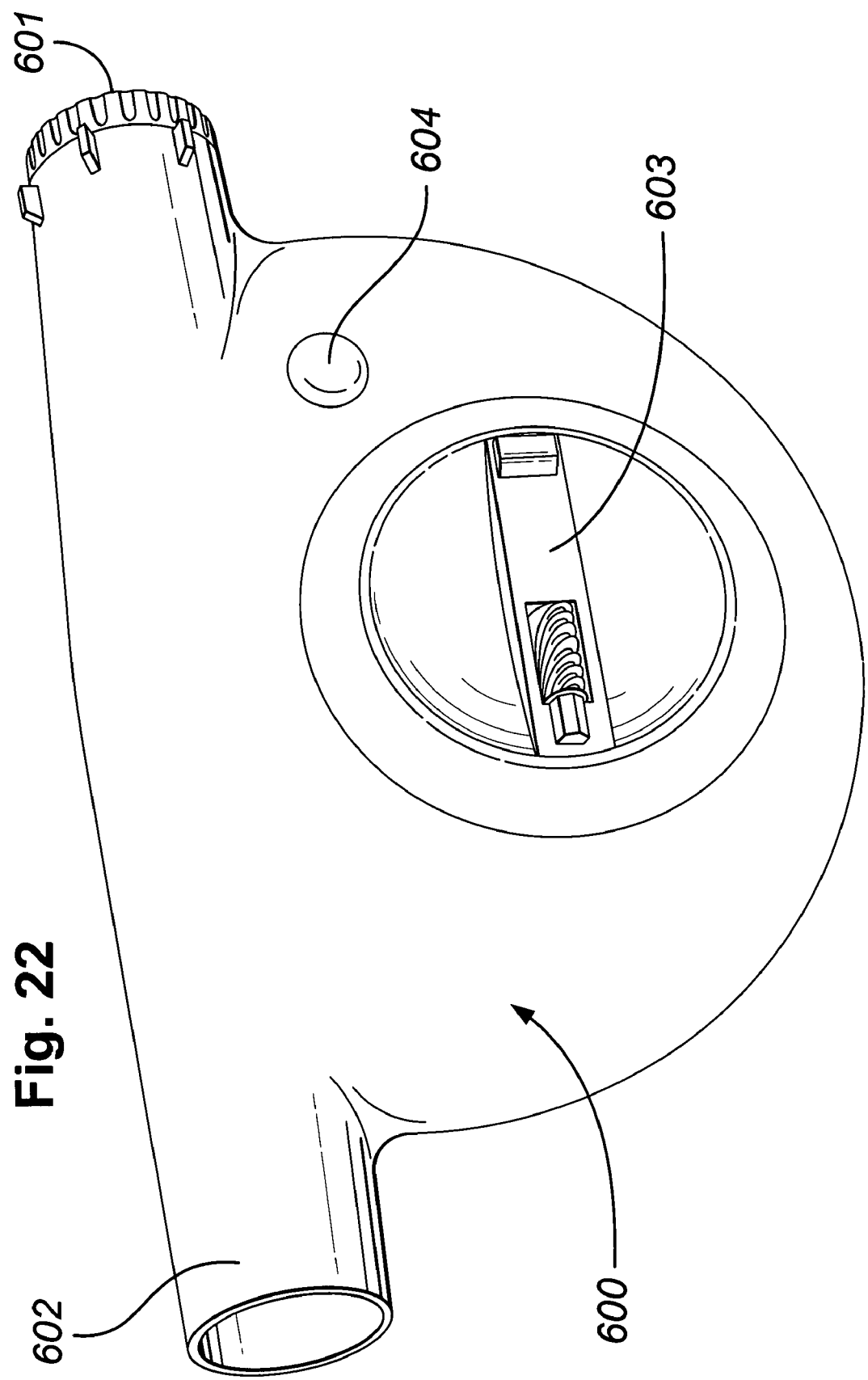
FIG. 22 illustrates a clockwork device.

The device illustrated in FIG. 22 comprises a housing 600 to a conduit having an inlet 601 and a mouthpiece 602. There is shewn a stowable wind-up handle 603 and an on-off button 604. Inside the housing and not shewn is a wind-up spring, a speed governor in the form of a sprung bob weight and a gear mechanism. The gear mechanism in turn operates a valve which may for example be a plug or disc valve as described herein. The gear mechanism operates to reduce the valve opening and closing cycle to the order of 20 Hz. As with the device described herein with reference to FIG. 21 the detachable head may comprise the mouthpiece but once again the whole device may be susceptible of repeated sterilization obviating a detachable head.

Figure 23:
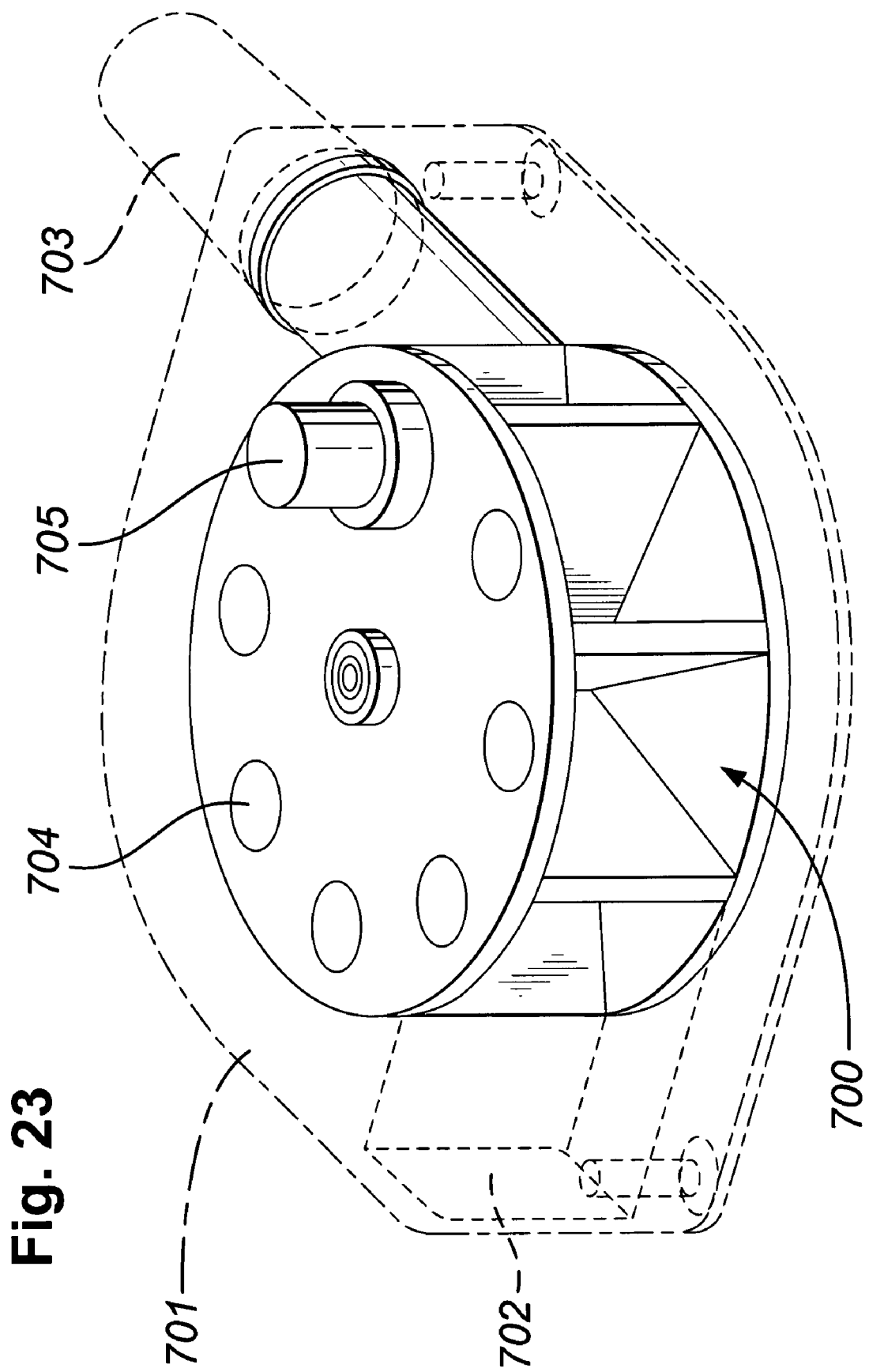
FIG. 23 is a schematic diagram of a device employing magnets.

Shewn in FIG. 23 is a rotary vane 700 in a housing 701, the housing having an inlet 702 and a mouthpiece 703. Set around the vane are a plurality of magnets 704 in the form of ferromagnetic discs while in the housing 701 is mounted a co-operating static magnet 705. In this case the co-operation of the rotating magnets 704 on the one hand and the static magnet 705 on the other provides the intermittent resistance to the flow of air in the conduit. This device may be electric motor driven in which case the housing 701 is preferably a head unit detachable from the power unit. Alternatively it may be clockwork or manual lever driven as per the devices herein described with reference to FIGS. 21 and 22.

An important feature of the device illustrated in FIG. 23 however is that it can actually be driven by the respiratory act itself. A degree of randomness in the breathing resistance cycle can be obtained by disposing the magnets irregularly around the vane.

Interchangeable discs may be provided for the different frequency requirements.

The invention claimed is:

1. A breathing device which comprises:
   a base unit;
   a head unit detachably attached to the base unit;
   a conduit in the head unit through which a user can breathe, the conduit having an axis; and
   a valve mounted in the conduit, the valve comprising a plug, the plug having an axis and arranged to rotate about its axis and periodically block the flow of air down the conduit, wherein the axis of the plug is located at an offset to the axis of the conduit.

2. A breathing device as claimed in claim 1 and having a mouthpiece which can fit over the mouth and/or nose of a user so that a user breathes through the mouthpiece.

3. A breathing device as claimed in claim 2 and wherein the mouth piece is detachable.

4. A breathing device as claimed in claim 1 and wherein there is a restrictor in the air inlet for restricting the flow of air.

5. A breathing device as claimed in claim 4 and wherein the restrictor is removable.

6. A breathing device as claimed in claim 4 and wherein the restrictor is adjustable.

7. A breathing device as claimed in claim 1 and wherein the valve produces regular periodic interruptions to the flow of air reaching the user and being breathed in by a user.

8. A breathing device as claimed in claim 7 and wherein the valve is a rotary valve which is driven by a motor in the base unit and the axle of the motor engages with the drive mechanism of the valve.

9. A breathing device as claimed in claim 8 and wherein the rotary valve comprises:
   a housing containing a fluid flow path with a central axis;
   a plug having a sealing face cooperating with said housing in the closed position to block the fluid flow path, and
   a support shaft arranged to carry said plug and being rotatable on an axis which is normal to and spaced from the axis of said valve seat and located outside of the flow path so that rotation of the said shaft moves said plug relative to said housing.

10. A breathing device as claimed in claim 8 and wherein the valve comprises two discs, at least one of which can be rotated relative to the other, with each of the discs defining at least one opening therethrough, the discs being positioned in the air flow so that, as at least one of the discs rotates relative to the other, the openings in the two discs are periodically coincident so as to form a continuous air flow passage.

11. A breathing device as claimed in claim 1 and wherein the head unit of the device can be removed and can be sterilised without the sterilisation of the base unit.

12. A breathing device as claimed in claim 1 and incorporating a battery.

13. A breathing device as claimed in claim 12 and wherein the battery is rechargeable.

14. A breathing device as claimed in claim 13 and incorporating means to manually charge the battery.

15. A breathing device as claimed in claim 1 and having means to vary the speed of the valve.

16. A breathing device as claimed in claim 15 and wherein the means to vary the speed of the valve is arranged to do so according to a fixed cycle.

17. A breathing device as claimed in claim 15 and wherein the means to vary the speed of the valve is arranged to do so randomly.

* * * * *